US00PP19366P2

(12) United States Plant Patent
Degenhardt

(10) Patent No.: US PP19,366 P2
(45) Date of Patent: Oct. 21, 2008

(54) ***MALVA* PLANT NAMED 'BLUE FOUNTAIN'**

(50) Latin Name: *Malva sylvestris*
Varietal Denomination: Blue Fountain

(75) Inventor: Dick Degenhardt, Boskoop (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 11/705,870

(22) Filed: Feb. 14, 2007

(51) Int. Cl.
*A01H 5/00* (2006.01)

(52) U.S. Cl. ..... Plt./263.1

(58) Field of Classification Search ..... Plt./263, Plt./263.1
See application file for complete search history.

(56) References Cited

PUBLICATIONS

UPOV–ROM GTITM, Plant Variety Database May 2000, GTI Jouve Retrieval Software, Citation for Malva 'Blue Fountain' one page.*

* cited by examiner

*Primary Examiner*—Kent L. Bell
*Assistant Examiner*—June Hwu
(74) *Attorney, Agent, or Firm*—C. A. Whealy

(57) ABSTRACT

A new and distinct cultivar of *Malva* plant named 'Blue Fountain', characterized by its tall and upright plant habit; large leaves; violet and dark violet bi-colored flowers; and good garden performance.

2 Drawing Sheets

Botanical designation: *Malva sylvestris.*
Cultivar denomination: 'Blue Fountain'.

BACKGROUND OF THE INVENTION

The present invention relates to a new and distinct cultivar of *Malva,* botanically known as *Malva sylvestris,* and hereinafter referred to by the name 'Blue Fountain'.

The new *Malva* is a naturally-occurring whole plant mutation of an unnamed selection of *Malva sylvestris,* not patented. The new *Malva* was discovered and selected by the Inventor within a population of plants of the parent selection in a controlled outdoor nursery environment in Boskoop, The Netherlands during the summer of 2002.

Asexual reproduction of the new *Malva* by terminal cuttings in a controlled environment in Boskoop The Netherlands since 2004, has shown that the unique features of this new *Malva* are stable and reproduced true to type in successive generations.

SUMMARY OF THE INVENTION

The cultivar Blue Fountain has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Blue Fountain'. These characteristics in combination distinguish 'Blue Fountain' as a new and distinct cultivar of *Malva:*

1. Tall and upright plant habit.
2. Large leaves.
3. Violet and dark violet bi-colored flowers.
4. Good garden performance.

Plants of the new *Malva* differ primarily from plants of the parent selection in the following characteristics:

1. Plants of the new *Malva* are shorter than plants of the parent selection.
2. Plants of the new *Malva* have larger leaves than plants of the parent selection.
3. Plants of the new *Malva* are shorter than plants of the parent selection.
4. Plants of the new *Malva* and the parent selection differ in flower color as plants of the parent selection have violet-colored flowers.

Plants of the new *Malva* can be compared to plants of the *Malva* cultivar Zebrina, not patented. In side-by-side comparisons conducted in The Netherlands, plants of the new *Malva* differed primarily from plants of the cultivar Zebrina in flower color. In addition, plants of the new *Malva* were taller than plants of the cultivar Zebrina.

BRIEF DESCRIPTION OF THE PHOTOGRAPHS

The accompanying colored photographs illustrate the overall appearance of the new *Malva,* showing the colors as true as it is reasonably possible to obtain in colored reproductions of this type. Colors in the photographs may differ slightly from the color values cited in the detailed botanical description which accurately describe the colors of the new *Malva.*

The photograph on the first sheet comprises a side perspective view of a typical flowering plant of 'Blue Fountain' grown in a container.

The photograph at the top of the second sheet is a close-up view of a typical flower of 'Blue Fountain'.

The photograph at the bottom of the second sheet is a close-up view of a typical leaf of 'Blue Fountain'.

DETAILED BOTANICAL DESCRIPTION

The aforementioned photographs and following observations, measurements and values describe plants grown in Boskoop, The Netherlands in an outdoor nursery during the summer and autumn. During the production of the plants, day temperatures ranged from 17° C. to 32° C. and night temperatures ranged from 10° C. to 19° C. Plants were about one year old when the photographs and the description were taken. In the detailed description, color references are made to The Royal Horticultural Society Colour Chart, 2001 Edition, except where general terms of ordinary dictionary significance are used.

Botanical classification: *Malva sylvestris* cultivar Blue Fountain.

Parentage: Naturally-occurring whole plant mutation of an unnamed selection of *Malva sylvestris,* not patented.

Propagation:

*Type.*—By terminal cuttings.

*Time to initiate roots.*—About three weeks at temperatures of 20° C.

*Time to produce a rooted young plant.*—About six weeks at temperatures of 20° C.

*Root description.*—Thick, fleshy; creamy white in color, close to 159D.

*Rooting habit.*—Freely branching, moderately dense.

Plant description:

*General appearance.*—Upright and columnar plant habit.

*Growth and branching habit.*—Moderately vigorous growth habit. Basal branching habit with about three lateral branches per plant.

*Plant height.*—About 38 cm.

*Plant width.*—About 25 cm.

*Lateral branches.*—Length: About 21 cm. Diameter: About 3 mm. Internode length: About 3.8 cm. Texture: Smooth, glabrous. Strength: Strong. Color: 144A.

Foliage description:

*Arrangement.*—Alternate; simple.

*Length.*—About 5.8 cm.

*Width.*—About 7.1 cm.

*Shape.*—Roughly orbicular; palmately lobed.

*Apex.*—Acute.

*Base.*—Hastate.

*Margin.*—Palmately lobed; lobes serrate.

*Venation pattern.*—Palmate.

*Texture, upper and lower surfaces.*—Smooth, glabrous.

*Color.*—Developing foliage, upper surface: 137B. Developing foliage, lower surface: 137C. Fully developed, upper surface: 137C; venation, 143A. Fully developed, lower surface: 138B; venation, 144C to 144D.

*Petiole.*—Length: About 7.2 cm. Diameter: About 2 mm. Texture, upper and lower surfaces: Pubescent. Color, upper and lower surfaces: 143A.

Flower description:

*Flower arrangement.*—Single rotate flowers arising from apical leaf axils. Flowers face upright or slightly outward. Flowers not persistent. Flowers not fragrant.

*Quantity of flowers.*—Freely flowering habit; about 36 flowers per plant will develop during the growing season.

*Flowering season.*—In The Netherlands, flowering is continuous from late June to early October.

*Flower longevity.*—Flowers last about ten days on the plant.

*Flower diameter.*—About 3.9 cm.

*Flower depth (height).*—About 1.5 cm.

*Flower buds.*—Length: About 8 mm. Diameter: About 7 mm. Shape: Roughly spherical. Color: 137D to 138A; towards the apex, N92A to N92C.

*Petals.*—Quantity per flower: Five in a single whorl. Length: About 2.1 cm. Width: About 1.7 cm. Shape: Obcordate. Apex: Emarginate to retuse. Base: Attenuate. Margin: Entire. Texture, upper and lower surfaces: Smooth, glabrous; satiny. Color: When opening and fully opened, upper surface: Close to N88C to N88D; towards the base and venation, 83A to 83B. Color becoming closer to N92C with development. When opening and fully opened, lower surface: Close to N88D; towards the base and venation, 83A to 83B.

*Sepals.*—Quantity per flower: Five, arranged in a single whorl. Length: About 9 mm. Width: About 5 mm. Shape: Elliptic. Apex: Acute. Base: Broad cuneate. Margin: Entire. Texture, upper surface: Smooth, glabrous. Texture, lower surface: Densely pubescent. Color: When opening, upper and lower surfaces: 143B. Fully opened, upper and lower surfaces: 143B.

*Peduncles.*—Length: About 2.4 cm. Diameter: About 1 mm. Strength: Strong. Angle: About 30° from vertical. Texture: Smooth. Color, upper and lower surfaces: 143A to 143B.

*Reproductive organs.*—Androecium: Stamen quantity per flower: About 25. Filament length: About 6 mm. Filament color: 79D. Anther length: About 0.5 mm. Anther shape: Narrowly oblong. Anther color: 164B. Pollen amount: Scarce. Pollen color: 157A. Gynoecium: Pistil quantity per flower: One. Pistil length: About 1 cm. Stigma shape: Terete. Stigma color: 85A to 85B. Style length: About 8 mm. Style color: 79D. Ovary color: 144B.

*Fruit/seed.*—Fruit and seed development have not been observed.

Disease/pest resistance: Plants of the new *Malva* have not been observed to be resistant to pathogens and pests common to *Malva.*

Garden performance: Plants of the new *Malva* have exhibited good tolerance to rain and wind and have been observed to tolerate temperatures ranging from about −20° C. to about 40° C.

It is claimed:

1. A new and distinct *Malva* plant named 'Blue Fountain' as illustrated and described.

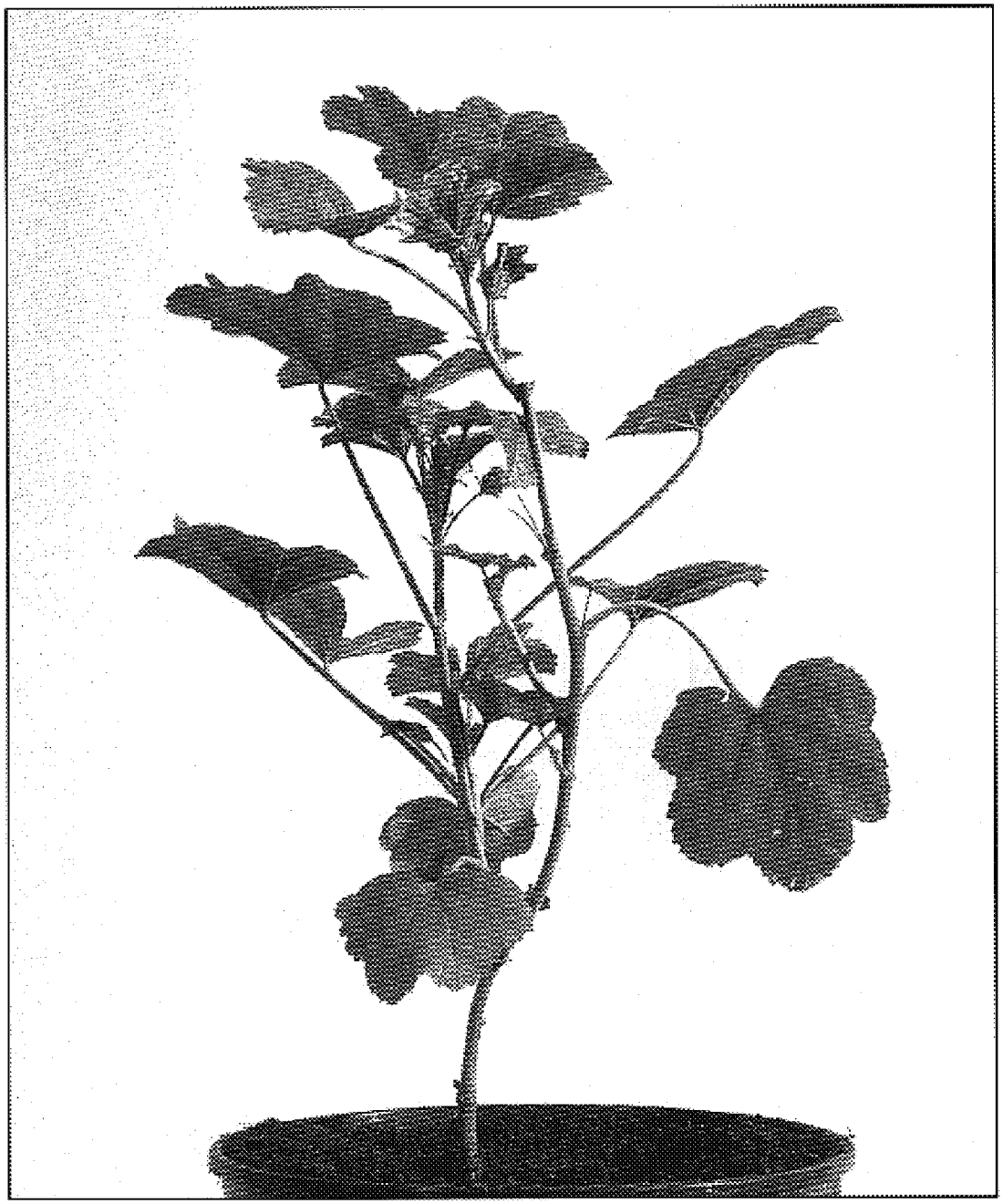

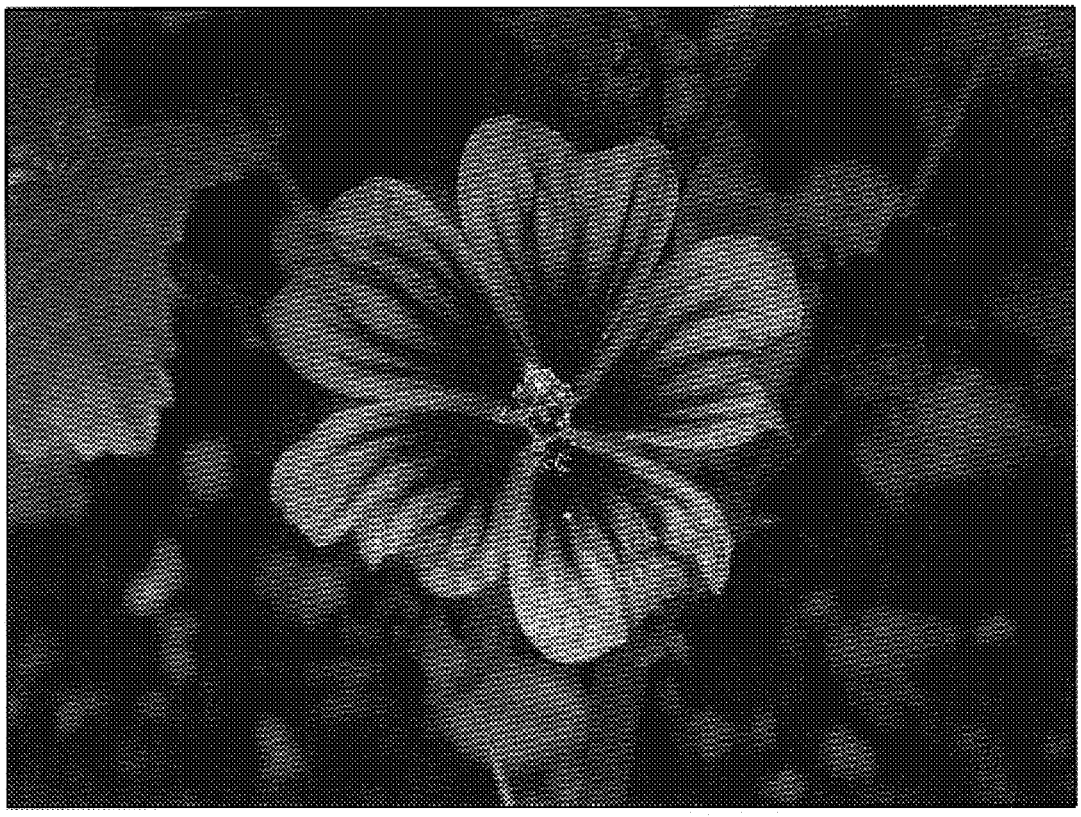
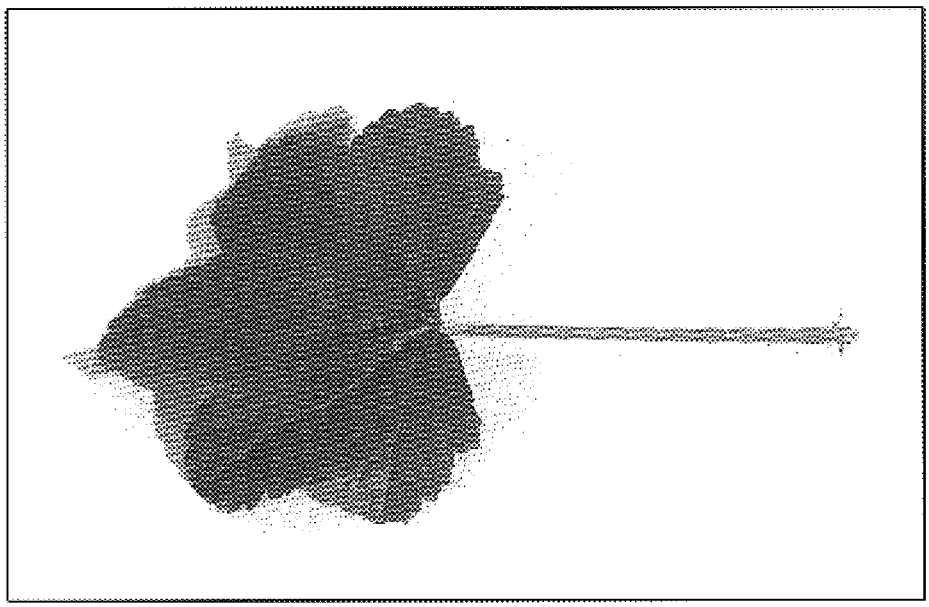

* * * * *